United States Patent
Wolter et al.

(10) Patent No.: US 7,977,404 B2
(45) Date of Patent: Jul. 12, 2011

(54) TOUGH, LONG-LASTING DENTAL COMPOSITES

(75) Inventors: Herbert Wolter, Tauberbischofsheim (DE); Carsten Gellermann, Gerbrunn (DE); Werner Storch, Hoechberg (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 863 days.

(21) Appl. No.: 11/912,145

(22) PCT Filed: Apr. 19, 2006

(86) PCT No.: PCT/EP2006/003585
§ 371 (c)(1), (2), (4) Date: Oct. 20, 2007

(87) PCT Pub. No.: WO2006/111373
PCT Pub. Date: Oct. 26, 2006

(65) Prior Publication Data
US 2008/0187499 A1  Aug. 7, 2008

(30) Foreign Application Priority Data
Apr. 20, 2005  (DE) .......... 10 2005 018 351

(51) Int. Cl.
- *A61K 6/08* (2006.01)
- *A61K 6/083* (2006.01)
- *A61K 6/093* (2006.01)
- *C07F 7/10* (2006.01)
- *C07F 7/18* (2006.01)
- *C07F 7/08* (2006.01)

(52) U.S. Cl. ...... 523/116; 523/115; 523/118; 433/228.1; 106/35; 977/919; 556/418; 556/419; 556/420; 556/436; 556/437; 556/438

(58) Field of Classification Search .......... 523/116, 523/115, 118; 106/35; 433/228.1; 977/919; 556/418, 419, 420, 436, 437, 438
See application file for complete search history.

(56) References Cited

U.S. PATENT DOCUMENTS

| | | | |
|---|---|---|---|
| 4,843,136 A | 6/1989 | Reiners et al. | |
| 5,233,006 A | 8/1993 | Wolter et al. | |
| 5,399,738 A | 3/1995 | Wolter et al. | |
| 5,414,093 A | 5/1995 | Wolter | |
| 5,717,125 A | 2/1998 | Wolter et al. | |
| 5,889,132 A | 3/1999 | Rheinberger et al. | |
| 6,106,606 A | 8/2000 | Gellermann et al. | |
| 6,852,822 B1 | 2/2005 | Bissinger et al. | |
| 2004/0023040 A1 | 2/2004 | Gellermann et al. | |
| 2007/0135572 A1 | 6/2007 | Wolter | |

FOREIGN PATENT DOCUMENTS

| | | |
|---|---|---|
| DE | 4133494 A1 | 4/1993 |
| DE | 19993177 A1 | 7/2000 |
| DE | 10018405 A1 | 10/2001 |
| WO | 0108639 A | 8/2001 |
| WO | WO 2005040249 A1 * | 5/2005 |

OTHER PUBLICATIONS

Meera, A. P.; Said, S.; Grohens, Y.; Luyt, A. S.; Thomas, S. Ind. Eng. Chem. Res. 2009, 48, 3410-3416. 2009 American Chemical Society.*

* cited by examiner

*Primary Examiner* — Mark Eashoo
*Assistant Examiner* — Michael Pepitone
(74) *Attorney, Agent, or Firm* — Gudrun E Huckett

(57) ABSTRACT

A dental composite containing a nanoparticulate filler has a resin matrix with structural element (Ib)

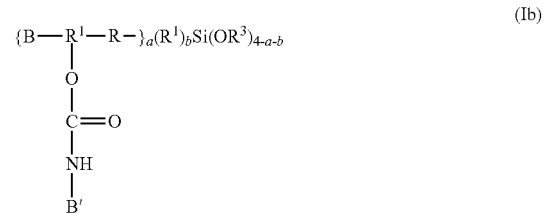

R is an open-chain and/or cyclic alkylene, arylene, or alkylene arylene with 1-10 C, optionally modified by oxygen, sulfur, carboxyl or amino, $R^1$ is an open-chain and/or cyclic alkylene, arylene, or alkylene arylene with 1-10 C, optionally modified by oxygen, sulfur, carboxyl or amino; R' is an open-chain and/or cyclic alkyl, alkenyl, aryl, alkyl aryl, or aryl alkyl with 1-20 C; B and B' are identical or different and are a straight-chain or branched organically polymerizable group with (meth)acrylate residue; $R^3$ are identical or different and a bond to another Si or hydrogen, alkyl with 1-10 C, or a bond to another metal atom; a is 1 or 2 and b is 0 or 1.

20 Claims, No Drawings

TOUGH, LONG-LASTING DENTAL COMPOSITES

BACKGROUND OF THE INVENTION

The present invention relates to dental composites with improved properties. The composites are produced by employing fillers and silicic acid hetero polycondensates, the latter at least partially comprised of a basic scaffold that has at least two (meth)acrylate residues per silyl unit wherein at least one of these (meth)acrylate residues is bonded by a urethane group. Starting materials (silane compounds) suitable for the present invention are disclosed among other compounds in DE 103 49 766.8 which, at the time of filing the instant application, had not been made publicly accessible.

In the past, a plurality of plastically processable composites based on organic monomers (for example, mono, di, tri or even higher methacrylates) in combination with commercially available fillers (for example, x-ray opaque dental glasses, highly dispersed silica, or the like) for use as dental restoration materials have been developed and have found acceptance in the market. However, the physical properties that are partially still unsatisfactory include e.g. abrasion that is too high, shrinkage during curing that is too high and leads to marginal gap formation particularly when subjected to chewing loads, x-ray absorption that is too minimal, aesthetic flaws as well as an allergenic potential (as a result of residual monomers). First significant advances in this regard have been achieved by employing inorganic-organic hybrid polymers (ORMOCER®) as a result of their dual character as matrix systems. Corresponding composites for dental applications are disclosed e.g. in patent application DE 41 33 494. Accordingly, it is possible to realize many important individual properties/requirements.

The realization of all important individual demands (shrinkage, aesthetics, marginal gap seal-tightness, abrasion resistance, bio-compatibility, x-ray opacity and optionally others) in combination, i.e., in one material type and at a significantly increased overall property el as a prerequisite for a significantly increased "service life" of restoration and prophylactic measures however has not been achieved with the materials currently available. Moreover, a further aspect increasingly gains importance, i.e., the bio-compatibility of the dental materials. For example, residual monomers that remain as a result of incomplete curing of the composite and that subsequently will slowly leak from the material can cause allergies in a patient. Moreover, often it would be desirable that the materials are already free of monomers in the state in which they are delivered to the dental office in order to prevent possible allergies in the dental assistant or the dentist.

It is an object of the present invention to find a remedy and to provide new composites as well as their use in the dental field, for example, for restorations, prophylactic measures, prosthetics, orthodontics.

This object is solved by providing dental composites that comprise:

(A) a matrix comprising a resin with the following structural element (Ib)

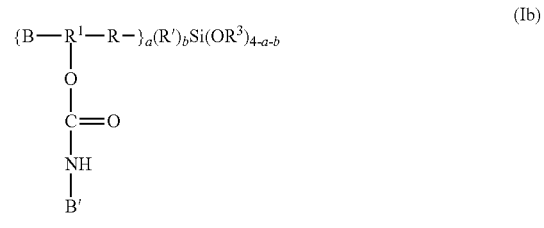

wherein the residues and indices have the following meaning;

R is an open-chain and/or cyclic alkylene group, arylene group, or alkylene arylene group with 1 to 10 carbon atoms, respectively, which can be interrupted by one or several oxygen or sulfur atoms or carboxyl or amino groups or can carry such atoms/groups at their end that is remote from the silicon atom;

$R^1$ is an open-chain and/or cyclic alkylene group, arylene group, or alkylene arylene group with 1 to 10 carbon atoms, respectively, substituted with the urethane group shown in the formula, that can be interrupted by one or several oxygen or sulfur atoms or carboxyl or amino groups or can carry such atoms/groups at one of their ends;

R' is an open-chain and/or cyclic alkyl group, alkenyl group, aryl group, alkyl aryl group, or aryl alkyl group with preferably 1 to 20 carbon atoms;

B and B' are the same or different; both residues have the meaning of a straight-chain or branched organically polymerizable group with at least one (meth)acrylate residue and thus at least 3 carbon atoms;

the residues $R^3$ are the same or different and at east one part thereof has the meaning of a bond to another silicon atom and represent otherwise a hydrogen atom, an alkyl group with 1 to 10 carbon atoms, or a bond to another metal atom that can be incorporated into silicic acid hetero polycondensates;

a is 1 or 2, and b is 0 or 1; and (B) is a nanoparticulate filler.

The dental material can be used as a composite material, fastening material, cement, filling material, adhesive, coating material, fissure sealant, tooth neck coating, crown or bridge material, or bonding.

Accordingly, excellent conditions are provided to realize today's desire for restorative and prophylactic measures with a significantly increased "service life" while providing optimal aesthetics and bio compatibility. The hybrid matrix which is the basis of the composites is comprised of resin systems containing (meth)acrylate groups that, for example, are disclosed in DE 103 49 766.8 already mentioned supra. They can be obtained either by hydrolytic condensation of silane compounds that can be produced by isocyanate addition to an OH-group containing compound. Alternatively, they can be produced by hydrolytic condensation of hydroxyl group containing silane compounds and subsequent reaction of the thus obtained resin with an appropriate isocyanate compound containing at least one (meth)acrylate group. A further important component of the composite in addition to the resin system is a nanoparticulate, optionally functionalized, filler that will be explained in more detail in the following.

The basis for the resin systems from which the composites according to the present invention can be produced are structural elements of the formula (Ib)

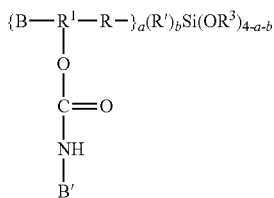

(Ib)

wherein the residues and indices have the following meaning:
R is an open-chain and/or cyclic alkylene group, arylene group, or alkylene arylene group with 1 to 10 carbon atoms, respectively, which in some cases can be interrupted by one or several oxygen or sulfur atoms or carboxyl or amino groups for can carry such atoms/groups at their end that is remote from the silicon atom.

$R^1$ is a substituted open-chain and/or cyclic alkylene group, arylene group, or alkylene arylene group with 1 to 10 carbon atoms, respectively, that, in some cases, can be interrupted by one or several oxygen or sulfur atoms or carboxyl or amino groups or can carry such atoms/groups at one of their ends and, as can be seen in the formula, is substituted with a urethane group that carries B'.

R' is an open-chain and/or cyclic alkyl group, alkenyl group, aryl group, alkyl aryl group, or aryl alkyl group with preferably 1 to 20 carbon atoms; in this context, reference is being had also to the further explanations in regard to the function of this group that can be found in connection with the definition of the formula (II) described infra.

B and B' can be the same or different; both residues have the meaning of a straight-chain, branched, or cyclic organic group that has at least one (meth)acrylate residue and therefore has at least 3 and preferably up to 50 carbon atoms. At least one of the residues B and B' in a preferred embodiment can have, in addition to the aforementioned first acrylate group or methacrylate group, a second or even a second and a third Michael system which, in turn, can also be, but must not be, an acrylate group or methacrylate group. Worth mentioning are residues B and B' that comprise as structural elements $C_2$ to $C_4$ alkanediols, the trimethylol propane group, the pentaerythrite group or the glycerol structure. B and B' can be acrylic acid ester groups and or methacrylic acid ester groups of trimethylol propane, of glycerine, of pentaerythrite, of $C_2$ to $C_4$ alkanediols, of polyethyleneglycols, of polypropylene glycols, or of bisphenol A, optionally substituted and/or alkoxylated, or can comprise these esters. Also preferred is also the embodiment in which B and B' represent only one (meth)acrylate group that is bonded by an ester bond of the carboxyl residue to the remaining molecule. B and B' can have a continuous carbon skeleton, the carbon chain(s) (main chain and/or side chain(s)) can however also be interrupted by hetero atoms or groups such as O, S, SO, NH, NHCO, PR, POR, CONHCO, COO, NHCOO or the like. The carbon skeleton of B and B' can be exclusively aliphatic, in particular with open and/or closed structures, B and B' can however also comprise one or several aromatic core(s) or condensed systems or triazine groups or the like, for example, bisphenol A structures or the like. Moreover, the groups or structures can be substituted in any way, for example, with acid groups, acid amide groups, ester groups or amino groups.

The residues $R^3$ bonded to the silicon atom can be the same or different. At least one part thereof must have the meaning of a bond to another silicon atom, optionally instead partially also to another metal atom that can be incorporated into the silicic acid hetero polycondensates. In many cases, not all residues $R^3$ will have this meaning, and in this case some of them instead will be a hydrogen atom, i.e., the silicon atom will carry one or several hydroxy groups. In the case that 4-a-b is 3, on average approximately 30% to 70%, i.e., up to approximately two of the three groups $OR^3$ can be hydroxy. When 4-a-b is 2, the number of groups $OR^3$ that are not crosslinked can be on average up to approximately 50%. In the case of 50%, on average one of the two groups is crosslinked with a further silicon atom or metal atom. In some of the aforementioned cases, some of the groups $R^3$ can have instead of hydrogen also an alkyl group with 1 to 10, preferably 1 to 4, carbon atoms. By means of the proportion of residues that represent bonds to further Si atoms or other metal atoms, the degree of condensation of the (partial) condensate is defined at least in as much as can be represented by the above formula (Ib).

a means 1 or 2, preferably 1, and b can be 0 or 1.

$R^3$ is preferably a residue with 1 to 4 carbon atoms and, particularly preferred, methyl or ethyl or a bond to a further Si atom.

These silicic acid polycondensates or partial condensates can be produced in a first synthetic pathway suitable for the present invention by hydrolytic condensation from silanes of the formula (Ia):

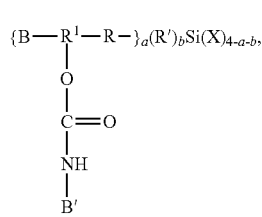

(Ia)

wherein the residues B, B', $R^1$ and R' have the meaning as provided supra for formula (Ib) and wherein X is a group that can undergo hydrolytic condensation reactions by forming Si—O—Si bridges. Groups X are referred to as inorganic crosslinking agents because by the hydrolytic condensation reaction a silicic acid polycondensate network can be formed. Accordingly, it is apparent to a person skilled in the art which meaning X can have. Preferably, X is a $C_1$-$C_{10}$ alkoxy group, even more preferred a $C_1$-$C_4$ alkoxy group, and especially preferred methoxy or ethoxy. X can also be, as needed, a halide such as Cl, hydrogen, hydroxy, acyloxy with preferably 2 to 5 carbon atoms, alkylcarbonyl with preferably 2 to 6 carbon atoms, or alkoxy carbonyl with preferably 2 to 6 carbon atoms. In some cases. X can also be NR" with R" being hydrogen, alkyl with preferably 1-4 carbon atoms or aryl with preferably 6-12 carbon atoms.

Preferred for the present invention are silicic acid polycondensates with the aforementioned structural element (Ib) wherein B has the meaning B"—Z— and Z is —O—$R^4$, —S—$R^4$, —NH—$R^4$, —C(O)O—$R^4$, —O—, —S—, —NH— or —C(O)O—. $R^4$ can have the meaning alkylene, arylene, or alkyl arylene with preferably 1 to 10 carbon atoms (in the case of groups without rings) or 6 to 14 carbon atoms (for groups with rings). B" is in this connection like B a straight-chain or branched organic group with at least one (meth)acrylate group and up to preferably 50 carbon atoms.

The silicic acid poly (partial) condensates with the structural element of the formula (Ib) can optionally also be derived from a mixture of different silanes of the formula (Ia) in which the residues B and/or B' have different meanings. In these condensates the residues B and/or B' do not have a uniform meaning. Since B in these condensates, on the one hand, can have the meaning as defined for B', but, on the other hand, can also have a meaning that is different therefrom, the formula (Ib) encompasses silicic acid poly (partial) condensates in which all residues B and B' have the same meaning; silicic acid poly (partial) condensates in which B and B' have a different meaning but all residues B and all residues B' represent the same residue, respectively; and silicic acid poly (partial) condensates in which the residues B' have a meaning different from B and the residues B and/or the residues B' each are mixtures of different residues. Alternatively, or in addition, these condensates can contain foreign metal atoms that can be incorporated by condensation into such systems, for example, boron, aluminum, germanium, tin, titanium or zirconium. The metals that are suitable for this purpose are known to a person skilled in the art. In the case of silicic acid poly (partial) condensates containing foreign metals the substances are referred to as hetero silicic acid poly (partial) condensates.

It should be mentioned that the components B and B' in the silicic acid (partial) condensates with the structural element (Ib) used in the present invention must not necessarily be present in stoichiometric ratios relative to one another as can be derived from the structural element itself. As can be taken in the following from the description and the examples, for example, the residue B' can be present in a substoichiometric quantity. In these cases, the poly (partial) condensate still contains free (or "capped" or "protected" as a result of rearrangement) hydroxy groups; this, as disclosed above, affects the viscosity behavior of the resin.

The structural elements of the present invention are therefore silanes and silicic acid poly (partial) condensates derived therefrom that comprise a partially or completely hydrolyzable/hydrolyzed and/or condensable/condensed silane residue, at least one urethane group and at least two residues that are in a branched arrangement and contain (meth)acrylate groups so that they are organically polymerizable wherein one of them is bonded by means of the aforementioned urethane group to the silicon atom. All three molecule parts can be utilized for the purpose of property modifications in accordance with the annual report of the Fraunhofer Institut für Silicatforschung 1992, pp. 61-72 and Polymer+Materials Research Symposium 1993, Bayreuth, pp. 14-17. In this connection, the additional organically polymerizable group that has been introduced via the urethane group provides an additional crosslinking possibility by means of the organic residues in comparison to the silicic acid polycondensates of DE 44 16 857 C1 so that harder polymers can be obtained.

As will be explained in the following in more detail, the silanes and the silicic acid poly (partial) condensates derived therefrom can be obtained from silanes that have a residue B as well as a hydroxy group that is bonded to a linker between this residue B and the silicon atom. They are disclosed in DE 44 16 857 C1. When comparing the systems that are obtained by direct condensation of such silanes with those of the present invention, it is apparent that the hydrophilicity of the matrix of the system according to the invention in comparison to that of the systems according to DE 44 16 857 C1 is reduced because none or, when some of the original hydroxy groups have not been reacted, only a reduced number of free OH groups are present so that wet-resistant (hydrolytically more resistant) less viscous resins with reduced sensitivity relative to moisture are obtained. On the other hand, by means of the variability of the residues B, B', R, $R^1$ and R' a high variability can be achieved that leads to special or new property combinations. A further advantage of the present invention resides in that condensates can be produced that are free of starting monomers and, based thereon, organic polymers (by polymerization of the organically polymerizable groups) with excellent mechanical properties and minimal shrinkage can be obtained that have viscosity properties ensuring excellent processing possibilities. Such polymers are referred to in the following as polymerisates when they are free of fillers and as composites when they are containing fillers.

By means of the organically polymerizable portions (primarily the (meth)acrylate groups) of the residues B and B' the aforementioned silicic acid polycondensates can be organically crosslinked. In this connection, because of the presence of at least two organically crosslinkable groups per silane molecule, a system is obtained that is generally free of starting materials whose organic proportion leads to an especially high mechanical strength as well as, surprisingly, an improved shrinkage behavior with reduced shrinkage. According to the invention, these systems can be used in combination with nanoparticulate filler and optionally additional fillers as dental composites with extremely advantageous properties.

Accordingly, based on the aforementioned resins, inorganic-organic polymers with excellent mechanical properties (for example, minimal shrinkage) are obtained that are completely or essentially free of the monomers used as starting materials, wherein the resins themselves as a result of, for example, their beneficial viscosity properties enable excellent processing possibilities. These polymers are provided in the form of composites (i.e., containing fillers, wherein at least one essential proportion of the filler or fillers are nanoparticulate fillers) and are suitable, as a result of their beneficial properties with regard to toxicological considerations (for example, because of their high bio-compatibility) in combination with high hydrolytic resistance and very minimal shrinkage, especially in the field of dentistry.

The composites according to the present invention can be adjusted with regard to rheological properties before curing as needed. For example, by adding monomeric additives (for example, reactive thinners) the flowability of the materials can be increased so that they are suitable as fissure sealers or the like. For other application purposes such as fillings prostheses, materials of higher viscosity are required instead. In this way, different applications in the dental field can be realized, for example, for the purposes indicated supra. The composites have a high abrasion resistance (with regards to wear caused by chewing and antagonist wear). As needed, a high x-ray opacity can be imparted in that they contain appropriate x-ray opaque fillers.

The compounds and (partial) condensates that are suitable for use in the present invention are obtainable, for example, based on the compounds of the formula II

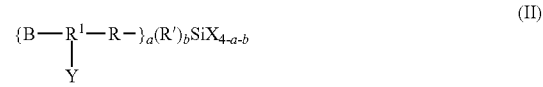

wherein B, $R^1$, R, R', X, a and b have the meaning as indicated for the formulas (Ia) and (Ib) and wherein Y is OH. The substituents or residues R' and X on the silicon atom can be selected arbitrarily. In the literature a lot has been reported in regard to the inorganic-organic materials containing silicon atoms, for example, those that are available commercially under the name "ORMOCER®", with respect to the respective properties that are imparted by the respective silane residues to the condensate or the organically polymerizable network so that in this connection no detailed explanations are needed. X indicates the hydrolyzable residues. With these groups that are also referred to as inorganic crosslinkers, in cooperation with optionally present organic crosslinkers, i.e., in particular the organically polymerizable groups of the residues B and optionally B', physical properties of the network that is formed can be adjusted, such as hardness or flexibility or thermal expansion coefficient. The groups R' that are usually not organically polymerizable, are referred to as network modifier; several properties can be affected with their selection. A person skilled in the art therefore is aware which meaning X can have. Preferably, X is a $C_1$-$C_{10}$ alkoxy group even more preferred a $C_1$-$C_4$ alkoxy group, and especially preferred methoxy or ethoxy. However, X can also be, as needed, a halogenide such as Cl, hydrogen, hydroxy, acyloxy with preferably 2 to 5 carbon atoms, alkyl carbonyl with preferably 2 to 6 carbon atoms, alkoxy carbonyl with preferably 2 to 6 carbon atoms, optionally also NR" with R" being hydrogen, alkyl with preferably 1 to 4 carbon atoms, or aryl with preferably 6-12 carbon atoms, or another suitable leaving group.

Compounds of the formula (II) are known. Compounds of the formula (II) can be produced, for example, according to DE 44 16 857 C1 in which B has the meaning B"—Z— wherein B" can also have the meaning of a straight-chain or branched organic group with at least one (meth)acrylate group and up to preferably 50 carbon atoms with the preferred embodiments for B as described. For example, when reacting epoxide silanes with compounds B"(AH) in which AH is a hydroxy group, a mercapto group, an amino group or carboxylic acid residue, a product is obtained in which Y is —OH and Z is —O—R", —S—R", —NH—R", —C(O)O—R", —O—, —S—, —NH— or —C(O)O—. R" has the aforementioned meaning. The reaction is realized usually in the presence of a suitable catalyst, for example, tertiary amines such as triethylamine or phosphines such as triphenylphosphine and optionally at elevated temperatures.

In the afore described reactions for producing the compounds of the formula (II), it is possible that isomers of these compounds are produced depending on the actually employed starting materials. This is in particular the case to a considerable amount when the residues X are alkoxy groups, primarily methoxy or ethoxy groups. Because in such isomers the group Y is partially involved in the isomerization/transesterification reaction, it is partially no longer free in these products. However, it was found that these byproducts can be utilized just as well as the compounds of the formula (II) place to different degrees and can be essentially suppressed. Therefore, in general a condensate with an Si—O—Si network is obtained.

The compounds of the formula (II) or their condensation products with liberated group Y are processed as needed (for example, separated, washed, isolated) and/or, if needed, dried. In particular it should be taken care optionally that no or if possible only few H-active contaminants are present in the reaction mixture in order to avoid in the reaction to be described in the following side reactions with the isocyanate. Subsequently, they are reacted with isocyanate containing at least one (meth)acrylate group and a product results in which a second (meth)acrylate group is present that is bonded by a urethane group —NH—C(O)O—.

When monomer compounds of the formula (II) are reacted, in general silanes of the formula (Ia) will be obtained. They can be subjected subsequently to hydrolytic condensation in order to obtain condensates of the formula (Ib).

The preparation of the silane compounds discussed above in connection with the afore described pathway for preparing the resins can be realized in different ways. In the following, some method variants will be explained in principle.

In a first embodiment of the invention, in a first step of the preparation a compound B"(COOH), wherein B" has the above meaning, is reacted with a silane in [$CH_2$—CH(O)]—R—Si(X)$_3$ containing an oxirane ring in which R and X have the meaning as set forth for formulas (Ia), (Ib) and (II). Preferably, X is a methoxy group, ethoxy group, propoxy group, or butoxy group. R can be, for example, —$CH_2$—O—$(CH_2)_3$. The reaction is realized preferably in the presence of a catalyst as explained above and at elevated temperatures. As described above, in this reaction, depending on the starting material and the reaction conditions, not only compounds of the formula (II) are produced but also, or even exclusively, condensation products (transesterification products), for example, by loss of an alcohol molecule or by formation of bridge bonds between the oxygen atom of the hydroxy group that is being formed (the group Y in the formula (II)) and a silicon atom, in accordance with the following schematic illustrating as an example the reaction of methacrylic acid with 3-glycidyloxypropyl trimethoxysilane ("glymo"):

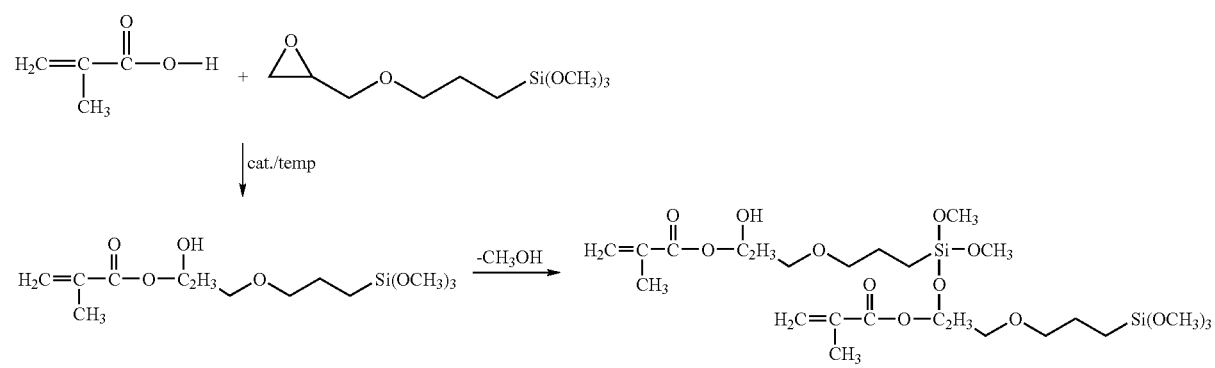

themselves for the production of the silicic acid poly (partial) condensates that are used to prepare the composites of the present, wherein a separation of the different products is not even necessary. It is instead sufficient to react the starting materials described for the preparation of the compounds of the formula (II) in the described way and to subsequently subject them to hydrolysis. Surprisingly, the group Y is then set free again while the back formation of SiOH groups takes The above schematic shows an intermolecular rearranged product. It should be clear that, of course, the products of intramolecular condensation or transesterification reactions can be used also.

The product or product mixture, inasmuch as the OH groups are not completely hydrolyzed, can be subjected to hydrolysis that effects inter alia condensation of the silane residues. Surprisingly, when X is an alkoxy group, free hydroxy groups on the silicon atoms are not necessary produced in significant quantities while the hydroxy group at the position Y is formed. As already described above in general, the formation of free hydroxy groups on the silicon atom can be adjusted and, as needed, can be suppressed essentially. Accordingly, a silicic acid polycondensate or partial condensate can be obtained that, to a very large extent, optionally predominantly, or even completely, contains the following structural element (III)

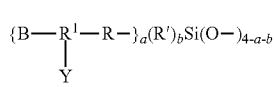

wherein the indicated residues and indices have the above explained meaning.

The above explained hydrolysis however will often not be necessary. This is so because the silylation of the hydroxy group can optionally protect it. When in the reaction mixture partially free and partially protected OH groups are present, it is easy to produce a condensate of the formula (Ib) in which the residues B' in relation to B are present in a deficient amount. That this may be desirable has been explained above.

In an alternative preparatory pathway for the hetero polysiloxane that can be used as a component of the dental material according to the present invention, the first step is the reaction of a compound B"(OH), wherein B" has the above meaning, with a silane $[CH_2—CH(O)]—R—Si(X)_3$ containing an oxirane ring in which R and X have the meaning indicated above for the formulas (Ia), (Ib), and (II), Preferably, X is a methoxy group, ethoxy group, propoxy group, or butoxy group, R can be, for example, $—CH_2—O—(CH_2)_3$. The reaction is carried out preferably in the presence of a catalyst as explained above and at elevated temperatures according to the following schematic illustrating as an example the reaction of HEMA (hydroxy ethyl methacrylate) with 3-glycidyloxypropyl trimethoxysilane ("glymo"):

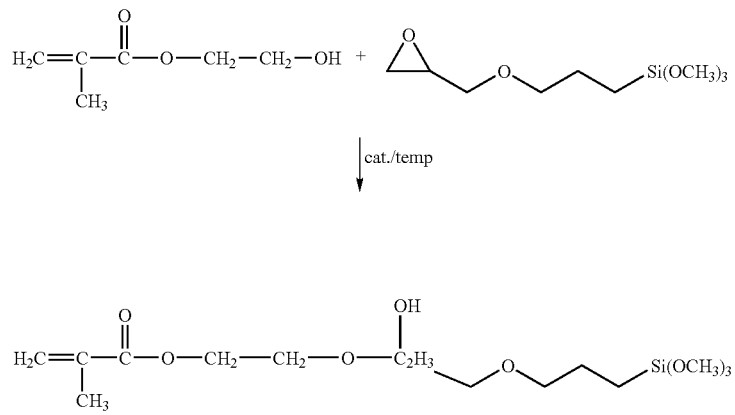

As explained above, in this reaction, depending on the starting material, not only a component of the formula (II) but also, or even exclusively, condensation products can be produced, for example, by loss of an alcohol molecule and formation of a bridge bond between the oxygen atom of the hydroxy group that is being formed (the group Y in the formula (II)) and a silicon atom, Accordingly the following transesterifications are possible for this reaction in principle.

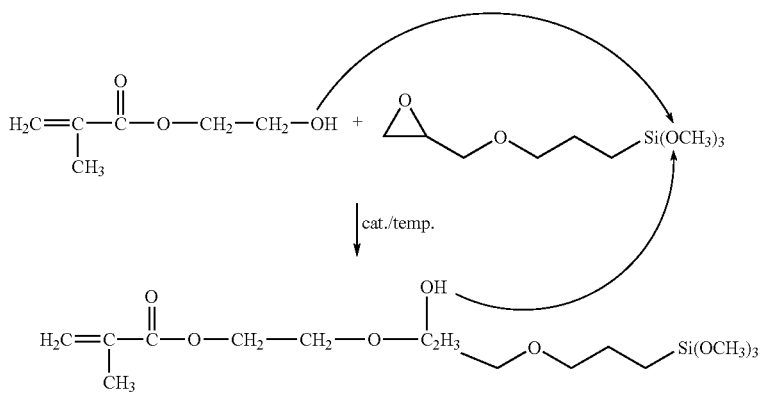

The next step of preparing the condensates can be realized as described in the following. The product of the first step is reacted with a compound B'NCO wherein B' has the above described meaning. In this ways a compound of the formula (Ia) or a condensate with the structural element (Ib) is produced.

The two-stage synthesis of the silane resins suitable for the purposes of the present invention will be explained in more detail in the following with the aid of a few schematics.

1. Hydroxy-functionalized dimethacrylate from DE 4416957

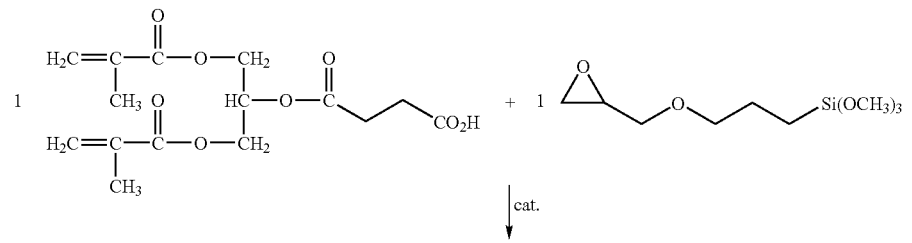

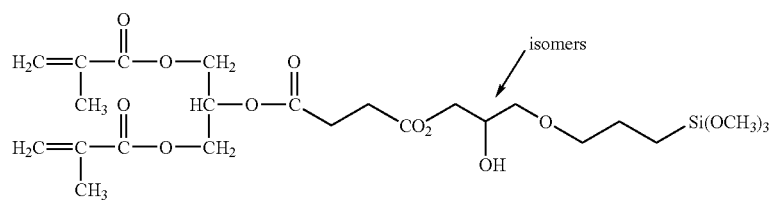

1a. Reaction of above hydroxy-functionalized dimethacrylates

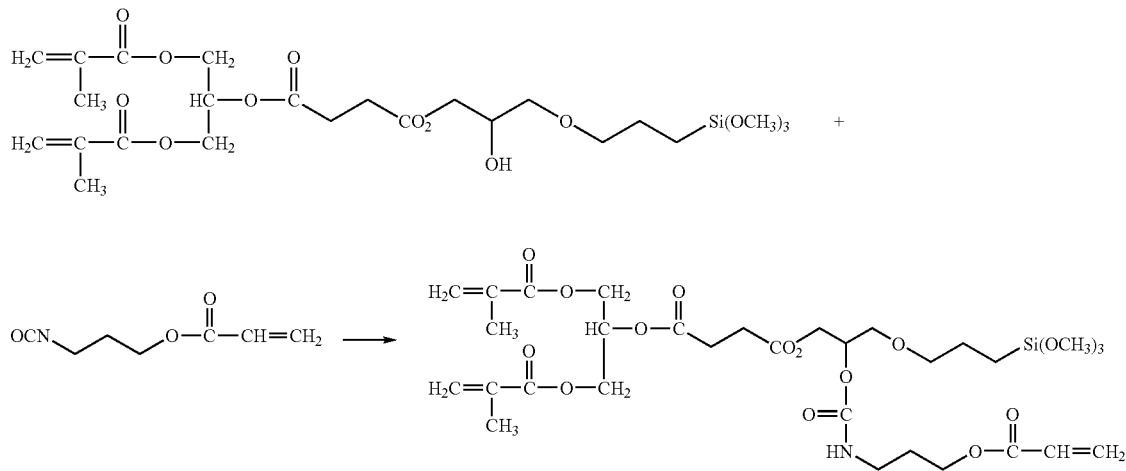

2. Hydroxy-functionalized dimethacrylate from DE 4416957

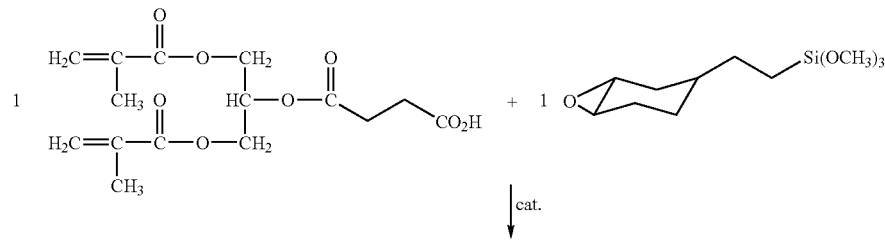

-continued
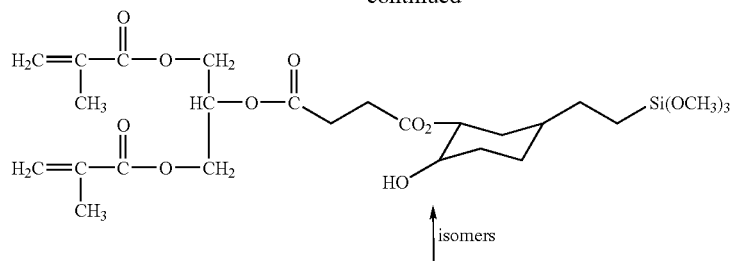
↑ isomers
2a. Reaction of above hydroxy-functionalized dimethacrylates
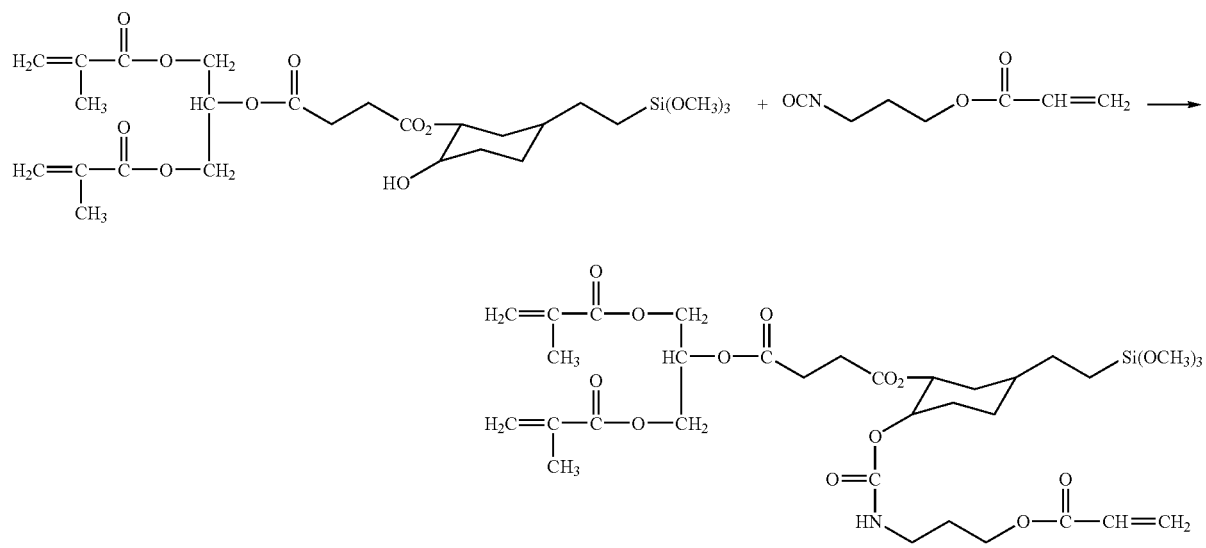
In the following, the preparation of compounds of the formula (Ia) will be explained moreover with the aid of a few selected reactions.
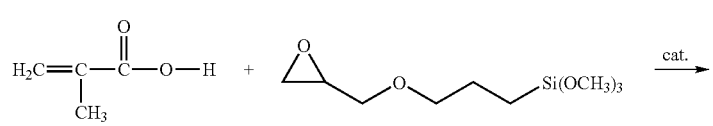
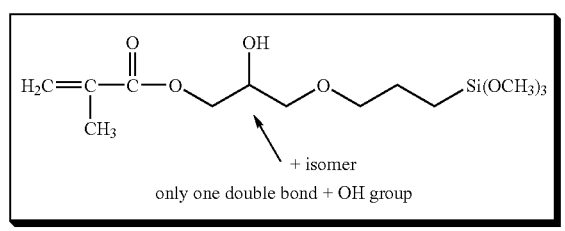
+ isomer
only one double bond + OH group
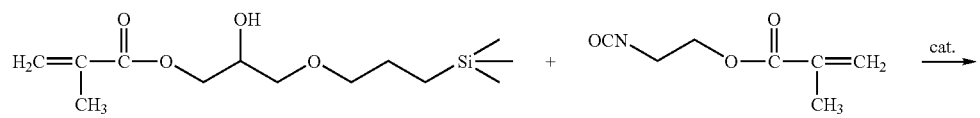

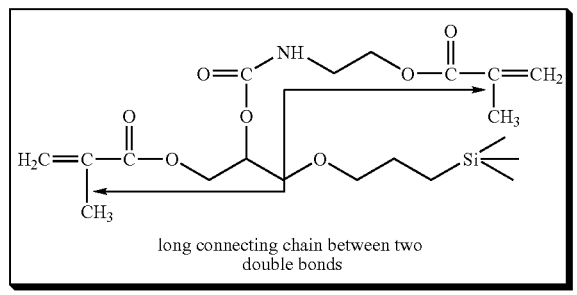
long connecting chain between two double bonds
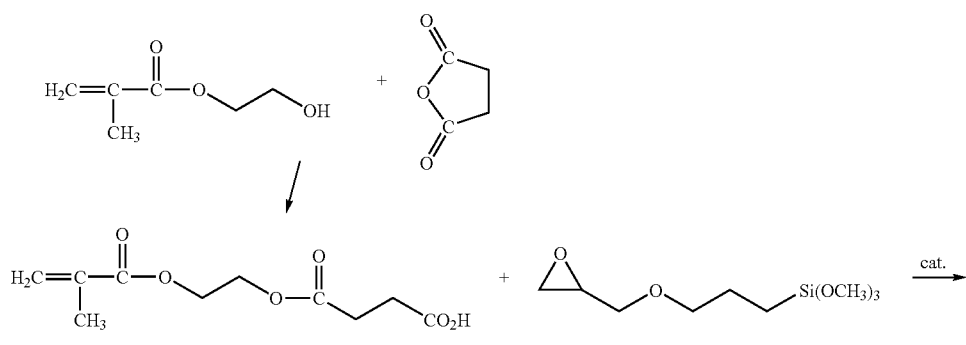
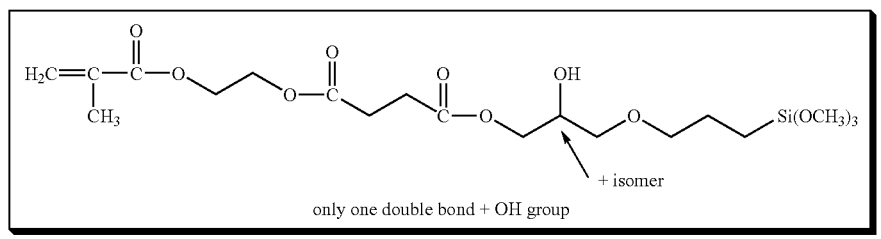
only one double bond + OH group
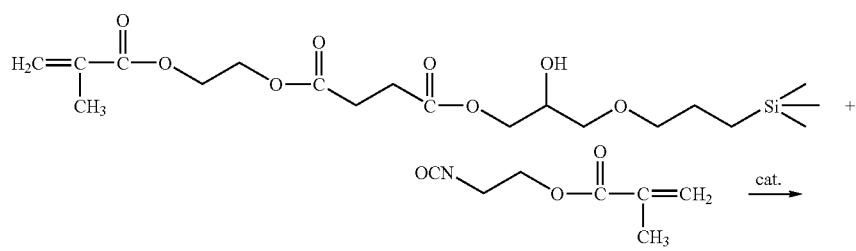
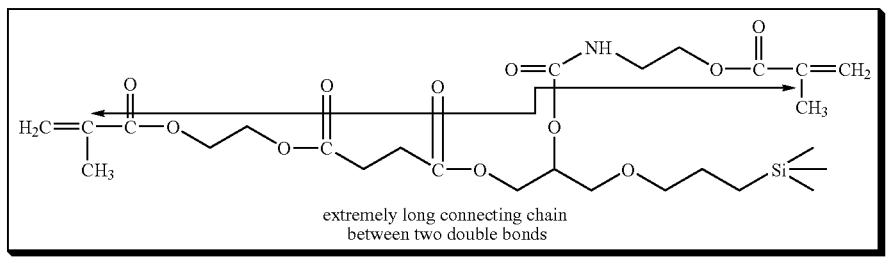
extremely long connecting chain between two double bonds
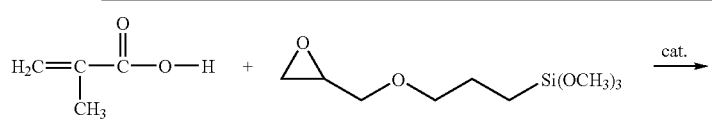
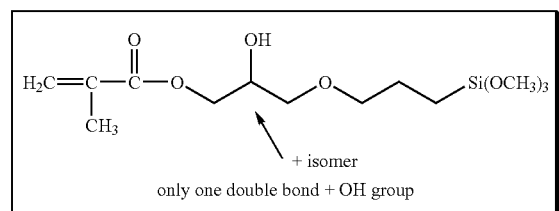
only one double bond + OH group -continued
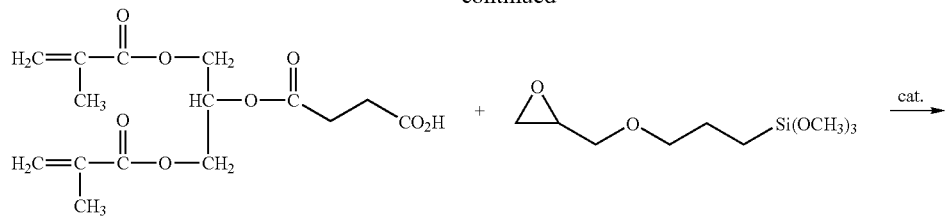
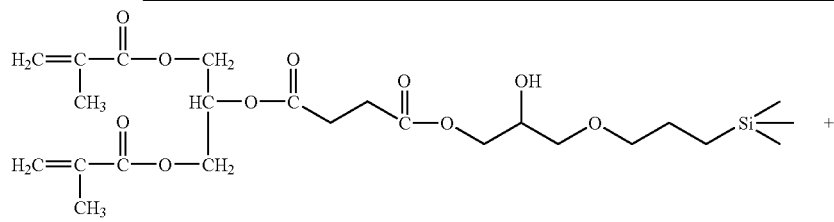
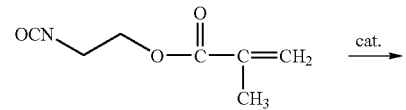
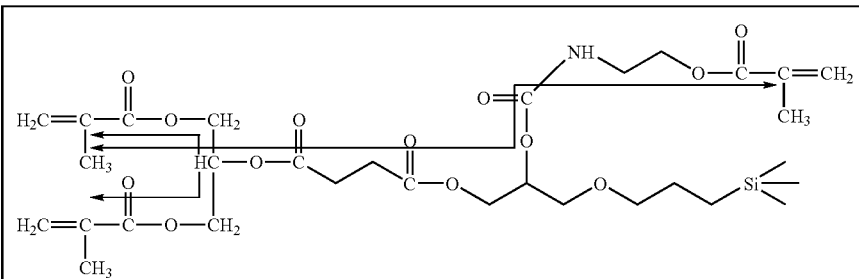
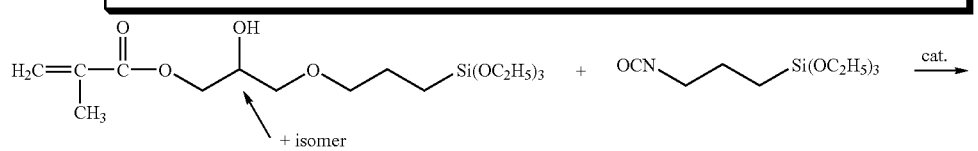
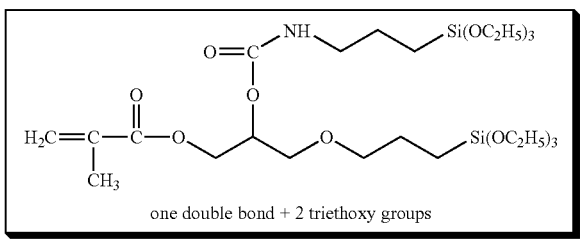
The above schematics illustrate that, according to DE 103 49 766.8, in the context of isocyanate addition silanes of a very variable structure can be produced. For example with the product of the reaction of (meth)acrylate with glymo that is known from DE 44 16 857 C1 silanes of the formula (Ia) can be produced that, depending on the employed reaction partner, can have relatively long or relatively short connecting chains between the double bonds of the residues B and B' (see upper half of the first page of schematics). The same patent also discloses the product of the reaction of hydroxyethyl-methacrylate (HEMA), succinic anhydride, and glymo. This product contains a single methacrylic acid residue as well as a relatively remote hydroxy group. Based on this, compounds with two methacrylate groups can be produced between which very long or extremely long connecting chains can be arranged. In the middle of the second page of schematics, the reaction of compounds with two groups containing double-bonds (here methacrylate groups) and positioned relatively close together as well as a third double bond-containing group (here also a methacrylate group, but it could be also a different double-bond containing group) farther removed from the two groups is illustrated by means of an example.

For the purposes of the present invention, silanes of the formula (Ia) or silicic acid poly (partial) condensates that are not yet completely condensed and have structural elements according to formula (Ib) are partially, largely or completely hydrolyzed or condensed alone or optionally also with further silanes and/or silicic acid (partial) condensates. For this purpose, on the one hand silanes and (partial) pre-condensates derived therefrom that are co-condensable but not co-polymerizable or those that also have a polymerizable groups are suitable. Of course, the additional components can be admixed at an earlier stage as long as they do not undergo undesirable side reactions with isocyanates. In this way, condensates with exclusively the structural units of the formula (Ib) according to the invention or inorganic networks with Si—O—Si units result that contain these structural units in combination with other units. Co-condensable or co-polymerizable compounds or (partial) pre-condensates can be preferably reacted in a molar ratio of up to 80%, relative to the monomer units (silyl residues or polymerizable compounds) of which the resulting resin or polymer is built. Especially preferred is an addition in a molar ratio of up to approximately 20%.

Co-polymerizable components can be added, instead or additionally, to the silanes of the formula (Ia) as well as not yet completely condensed silicic acid poly (partial) condensates with structural elements of the formula (Ib); the co-polymerizable components are, for example, compounds that can be polymerized by radical and/or ionic and/or covalent-nucleophilic polymerization. Compounds to be added that can be polymerized by radical polymerization are, for example, those with C═C double bonds such as acrylates or methacrylates wherein the polymerization is realized by means of the C═C double bonds. Ionically polymerizable compounds to be added contain, for example, ring systems that can be polymerized by cationic ring-opening polymerization for example, spiroorthoesters, spiroorthocarbonates, bicyclic spiroorthoesters, monoepoxides or oligoepoxides or spirosilanes, as those known e.g. from DE 41 25 201 C1. It is also possible to add compounds that can polymerize ionically or by radical polymerization, for example, methacryloyl spiroorthoester. The latter can be polymerized by radical polymerization by means of the C═C double bond and cat-ionically by ring-opening polymerization. The preparation of these systems is disclosed, for example, in Journal f. prakt Chemie, Vol. 330 (2) 1988, pp. 316-318. Moreover, it is possible, for example, to add other known silane-bonded cyclic systems that can also be incorporated by polymerization. Such systems are, for example, those that contain epoxides. Such systems are disclosed in connection with the preparation of spirosilanes in DE 41 25 201 C1. The aforementioned components are incorporated by polymerization during the polymerization reaction of the resins by means of their organically polymerizable groups so that a copolymer resin of the silanes and copolymers according to the invention is obtained whose silane groups are hydrolytically condensed with one another or with other groups. The aforementioned components can be preferably added in a molar ratio of up 20%, relative to the monomer units (silyl residues or polymerizable compounds) of which the resulting resin or polymer is built. However, it is especially preferred to keep the composites of the present invention and thus also the basic organically polymerizable resins free of monomers.

As mentioned above, in an alternative synthetic pathway for preparing the resin systems according to the present invention, the compounds of the formula II can be used which are first hydrolytically condensed before the reaction with a (meth)acrylate group-containing isocyanate is carried out. With the exception of this reversal, the aforementioned explanations also apply to this pathway of the preparation of the resin system.

The silicic acid poly (partial) condensates with structural elements of the formula (Ib) that are utilizable for the purposes of the present invention have, when Y is reacted completely or at large proportions, a low hydrophilicity of the matrix and therefore will absorb only little water in a moist/wet environment. Their wet strength is improved. The residues B and B' can be incorporated alone or in mixtures and/or co-condensates with other components as mentioned above into organic polymer structures or they can be crosslinked as such by these groups. As a result of the additional organic crosslinkable group or the additional silyl group that carries B', a general increase of the strength of the crosslinked products can be achieved. In particular, composites that are filled at a low level or high level, are obtainable that are made from resins with relatively minimal viscosity and that have a very minimal shrinkage. Their suitability as dental compounds should be underscored in particular, especially in configurations that are free of monomers and are thus toxicologically/allergenically innocuous and have generally moreover a high wet strength as well as further advantageous properties as mentioned already supra.

For obtaining the dental composites the silicic acid poly (partial) condensate with structural elements according to formula (Ib) is mixed before organic curing with one or several additives and/or fillers.

An important component in this regard are nanoparticulate fillers or a combination of such fillers of different size or different composition, optionally in combination with further known fillers such as particulate dental glasses, for example, Ba—Sr aluminumborosilicates. The term "nanoparticulate" is to be understood as the fillers having a diameter or having a greatest diameter in the range of less than 1,000 nm. In the case that the fillers have a relatively broad particle size distribution, at least 90% of the mass of the filler should be below this limit. According to the present invention, the term "nanoparticulate" filler is meant to include also sub-nanoparticulate fillers whose size can extend down to the size of the so-called clusters. Preferred are nanoparticulate fillers with approximately spherical shape. Even more preferred are fillers with diameters in a range of 10 nm to 400 nm, even more preferred in a range of 10 nm to 100 nm. It is moreover preferred to employ each individual filler with a very narrow particle size distribution.

The nanoparticulate fillers can be present individually, i.e., in isolated form, as agglomerates, aggregates, or polymer resins. Preferred is that they are used in a non-agglomerated, non-aggregated form.

The materials for the aforementioned fillers are not critical and are selected as needed. Well suited are, for example, those fillers that are used in the publications DE 196 43 781, DE 100 41 038, or DE 100 18 405. Well suited are $SiO_2$ particles that can be obtained in accordance with known sol/gel methods and that then have a very narrow diameter distribution. These but also nanoparticles of different composition can be surface-modified, for example, silanized, in order to match their surface properties to those of the matrix.

The nanoparticulate fillers can be used alone or in combination with other fillers for the purposes of the present invention. Employable as additional fillers are, for example, macrofillers (for example, made from glass, ceramics, or quartz, particle sizes between 2 µm to 50 µm), homogenous microfillers (for example, made from pyrogenic silica, particle sizes approximately 0.02 µm to 0.06 µm, preferably approximately 0.04 µm), inhomogeneous microfillers (for example, a portion of the pyrogenic silica is present as chipped polymerisate), hybrid fillers (mixtures of macrofillers and microfillers) or very fine hybrid fillers (for example, mixtures of aerosil and Ba glass or Sr glass with particle sizes in the range of approximately 1 µm to 5 µm). Well suited for the present invention are, for example, dental glasses with particle diameters of approximately 0.4 µm to 20 µm, preferably of approximately 1 µm to 5 µm.

The ratio of fillers relative to one another can be selected arbitrarily. Beneficial are weight proportions of the nanoparticulate fillers of approximately 5 wt. % to approximately 60 wt. % relative to the total weight of the fillers in the composite. Especially beneficial are proportions of more than 5 wt. % to 30 wt. %. In such embodiments, the nanoparticulate fillers can be located in the cavities or gaps of closed packed, possibly even approximately close (sphere) packed, larger filler particles, in particular when the larger filler particles have an approximately spherical shape. It was found that when using proportions in this range, particularly highly filled composites can be obtained that have a particularly minimal shrinkage and particularly high abrasion resistance.

Depending on the desired application, the filler can be added in very different total quantities. For example, on the one hand, it can be present in a proportion of 50 wt. % of the composite or even significantly higher and in particular in a proportion of 70 wt. % to 90 wt. % of the composite wherein higher or highest filled composites are required for example, for fillings or the like; on the other hand, for lower-level or low-level filled compositions, e.g., fissure sealants, coatings for tooth necks, the filler is present in a proportion of less than 50 wt. %, e.g., 1 wt, % to 50 wt. % and preferred approximately 1 wt. % to 20 wt. %.

In regard to obtaining high contents of fillers and excellent processing (for example, reducing the viscosity) optionally the use of filler pre-polymerisates is possible also, i.e., nanoparticulate and/or conventional fillers that are coated with a polymer matrix (in accordance with the present invention or a different one for example, a purely organic one) that are present in the form of cured composite spheres or composite chips.

Depending on the provided special application, the composite can also have added to it suitable additives such as initiators, coloring agents (dyes or pigments), oxidation inhibitors, polymerization inhibitors (for preventing a premature polymerization), leveling agents, UV absorbers, stabilizers, microbicidal agents, or the like as they are known to a person skilled in the art. Examples of polymerization initiators are initiators for radical polymerization and in particular for thermal curing such as peroxides (for example, dibenzoyl peroxide) or photo initiators such as benzophenone, camphor quinone, or combinations of α-diketones with amines as reducing agent, as e.g. disclosed in DE 199 03 177 C2. For dual curing of systems that are polymerizable by radical polymerization and cationic polymerization, diaryliodonium salts or tiarylsulfonium salts can be added in particular; the aforementioned publication also provides examples therefor.

The resulting plastically processable composites are distinguished thus in that they can have very variable filler contents and, at the same time, can be processed excellently. This enables advantageously their use in the field of dental restoration/prophylaxis (for example, for fillings, fissure sealants, and the like). The cured composites show inter alia a high strength and a high E modulus that can be matched or approximated to the respective application (for example, dentine has an E modulus of approximately 18 GPa or in liquid approximately 10 GPa). The same holds true for the thermal expansion coefficient α that for dentine is approximately at $8 \times 10^{-6} K^{-1}$. Moreover, they have a drastically increased abrasion resistance which keeps wear by chewing very minimal. Moreover, surprisingly they shrink upon curing (the organic crosslinking action) only minimally, as mentioned above (see examples). Moreover, they have, when required, high x-ray opacity which is achievable primarily by incorporating appropriate x-ray opaque fillers, in particular the aforementioned dental glasses and nano-particulate fillers of which many have a high x-ray opacity. Details in this regard are known to a person skilled in the art. For example, an exchange of $SiO_2$ particles for $SiO_2/SnO_2$ particles provides a significant increase of x-ray opacity. And finally, the composites according to the invention provide excellent aesthetics because the basic resin in a large number of embodiments is essentially colorless or translucent, which is self-evident in particular based on matched/approximated refractive indices of resin and filler particles and based on the particle distribution in their size.

The filled dental composite (i.e., the organically not yet crosslinked filled resin), after it has been applied in accordance with the indicated purpose, for example, applied to a dental cavity or filled into a mold that corresponds to a future prosthesis, can be organically crosslinked in a suitable way and thus cured. In this connection, primarily an organic polymerization of the (meth)acrylate groups is suitable. This is a radical polymerization that usually is carried out by adding radical starters as mentioned above and optionally known activators with exposure to light such as light in the visible range (blue light, dental curing light), i.e., photochemically, thermally, or redox-induced. Depending on the further additives added to the resin, as mentioned above, additional photo chemical, thermal, or chemical (for example by means of self-curing two-component reactions, anaerobic, redox, ionic, covalent-nucleophilic) induced reactions can take place by means of which the resin matrix will be crosslinked to an even narrower mesh structure. For example, the combination of self curing action with, for example, photoinduced or thermal curing is possible.

The composites according to the present invention exhibit as a result of the components that can be mutually matched to one another not only excellent data with regard to the individual properties but also an excellent overall profile of properties and thus significant advantages relative to the classic composites based on methacrylate-containing monomers (see, for example, composite 1 and 2 in the table of Example 3 infra). This is so because the matrix with regard to rheological properties and strength can be adjusted optimally to the field of application while the nanoparticulate fillers can be optimally selected with regard to their diameter, their x-ray absorption, their surface functionality and the like. Composites result with filler contents that can be higher than in the "classic" materials and, in this connection, can have a very high volume proportion in the composite with extremely minimal shrinkage, with (abrasion) strengths that match that of the neighboring natural materials, in general without this requiring that thinners (i.e., monomers) be added for processing.

can be monitored by the drop in carboxylic acid concentration by means of acid titration as well as epoxide conversion by means of Raman spectroscopy/epoxide titration. The characteristic band of the epoxide group of epoxy silane appears in the Raman spectrum at 1,256 cm$^{-1}$. The epoxide conversion or carboxylic acid conversion is at $\geq$99% or $\geq$89% (→because 1:1.1 excess carboxylic acid).

2nd Stage: Hydrolysis/Condensation

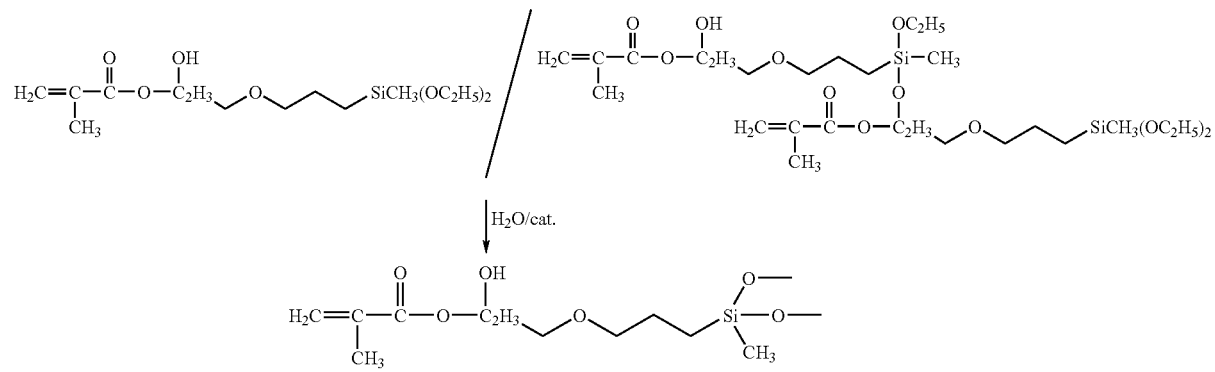

In the following the invention will be explained with the aid of exemplary embodiments in more detail.

DESCRIPTION OF PREFERRED EMBODIMENTS

Example 1

Prior Art

This example explains the preparation of a monomer-free resin system that contains free OH groups, based on a component of the formula (II) with b equal 0; the latter is disclosed also in DE 103 48 766.8

1st Stage: Reaction of 3-Glycidyl Oxypropyl Trimethoxysilane (Glymo) with Methacrylic Acid (MAS)

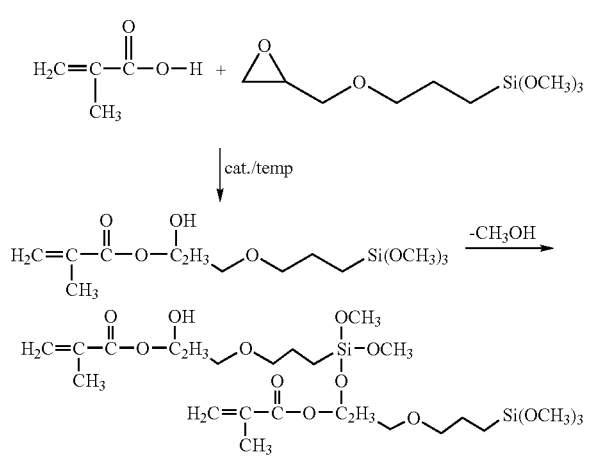

To an amount of 199.1 g (0.802 mol) 3-glycidyloxypropyl trimethoxysilane in a dry atmosphere (oxygen) triphenylphosphine as a catalyst, BHT as a stabilizer, and subsequently 75.76 g (0.88 mol) methacrylic acid are added dropwise and stirred at 85° C. (approximately 24 h). The reaction After adding acetic ester (1,000 ml/mol silane) and H$_2$O for hydrolysis with HCl as a catalyst, the reaction mixture is stirred at 30° C. The course of hydrolysis can be monitored by water titration, respectively. Processing is done after approximately several days of stirring by extracting several times with aqueous NaOH and subsequent extraction with water and filtration by means of a hydrophobic filter. Then, solvent is removed by means of a rotary evaporator and subsequently by oil pump vacuum in order to remove alcohol and water. A resin is obtained that without use of so-called reactive thinners (additional liquid monomers) is liquid and has a very minimal viscosity (approximately 4-6 Pa·s at 25° C. (strongly dependent on the precise hydrolysis and processing conditions). The CO$_2$H contents was measured to be 0.00 mmol/g, i.e., the resin contains no free monomeric methacrylic acid molecules anymore.

Example 2

This example explains the reaction of the resin system of Example 1 with isocyanate.

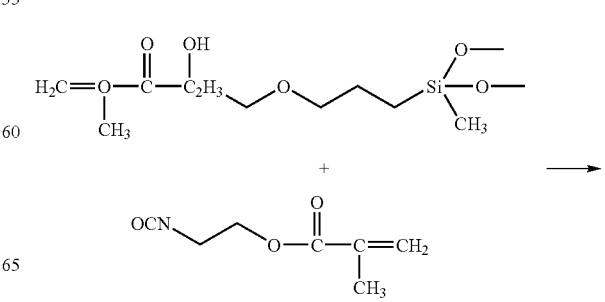

-continued

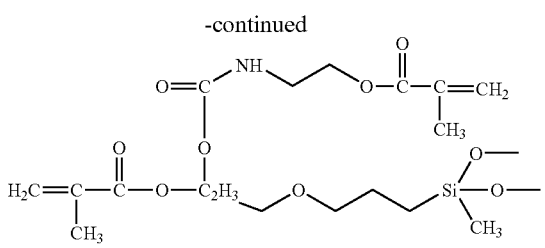

To an amount of 73.9 g (0.28 mol) of the above resin in a dry atmosphere (oxygen) at room temperature with stirring 30.41 g (0.20 mol) methacrylic acid isocyanate ethyl ester was added dropwise and the mixture stirred at 30° C. The reaction can be monitored by decrease of the OCN band by means of IR spectrum. The characteristic band for the OCN group appears in the IR spectrum at 2,272 cm$^{-1}$. A viscous resin resulted having a viscosity of approximately 18-25 Pa·s at 25° C. (strongly dependent on the precise synthesis and processing conditions in particular also of the pre-stages).

IR data: $v_{(OH \leftarrow educt)} \approx 3{,}500$ cm$^{-1}$ (residual OH because the reaction was carried out with only 0.7 mol proportions of methacrylic acid isocyanate ethylester)

$v_{(NH \leftarrow urethane)} \approx 3{,}373$ cm$^{-1}$ $v_{(C=O \leftarrow methacrylate/urethane)} \approx 1{,}721$ cm$^{-1}$ $v_{(C=C \leftarrow methacrylate)} \approx 1{,}638$ cm$^{-1}$ In the following, some properties of the matrix system according to Example 1 (without reaction with isocyanate) are compared with those of the matrix system according to Example 2.

|  | Matrix System (Example 1) | Matrix System (Example 2) |
| --- | --- | --- |
| break strength [MPa] stored 1.5 days at 40° C. under dry conditions | 70-80 | 103-115 |
| E modulus [GPa] | 1.7-1.9 | 2.2-2.5 |
| shrinkage [vol-%] (15 min) | 54 | 4.2-4.6 |
| cytotoxicity [% active cells] after 24 h | 95-97 | 97-102 |

The comparison shows that the organic components of the matrix system according to the invention has improved properties in comparison to the resins used in the prior art; strength and the E modulus are significantly increased and shrinkage is significantly reduced.

Example 3 and Comparative Examples a) Composite Preparation and Characterization The incorporation of different filler types into the described resin system after addition of conventional photo initiators as well as further dental additives is carried out in accordance with conventional methods by using different mixing device types at different temperatures and optionally under vacuum.

The resulting composites are placed into a rod mold (2×2×25 mm$^3$). The methacrylate groups are reacted by a photo-induced radical polymerization so that the respective composite is cured. By means of a 3-point bending test after 1.5 days of storage in air or water at 40° C. the E modulus as well as the break strength (at room temperature) of the resulting rods are determined.

The shrinkage values of the composites are determined by means of buoyancy flotation method (composite 3) or by means of mercury dilatometer (comparative composites 1 and 2) for a photo-induced radical polymerization.

The in vitro cytotoxicity test is carried out by means of growth inhibition test in a microtiter plate on 3T3 mouse fibroblasts with composite eluates at the MHH Hannover.

The abrasion was determined in a 3-media abrasion machine according to the ACTA method.

The x-ray opacity was measured according to EN ISO 4049 with an x-ray device type Polydoros SX80 of the Siemens company and ultraspeed films of the Kodak company. The determination of the degree of firm blackening was done by means of a dosimeter Lullus 1.21 (photo densitometer) of the Wellhöfer company.

The thermal expansion coefficient α was measured and evaluated by means of a dilatometer 402 E/7 of the Netzsch company in a temperature range of 5° C. to 50° C.

b) Composite Data

In the following, the material characteristic data of two commercially available filler composites (composites 1 and 2) are listed in comparison to a composite 3 based on the matrix system according to Example 2 in combination with standard fillers and a composite 4 according to the present invention based on the matrix system according to Example 2 with nanoparticulate fillers.

|  | Composite 1 | Composite 2 | Composite 3 | Composite 4 |
| --- | --- | --- | --- | --- |
| Filler mixture | Ba—Al borosilicate glass/highly dispersed silica | Ba—Al borosilicate glass/Ba—Al fluorosilicate glass/ytterbium trifluoride; highly dispersed silica | Ba—Al borosilicate glass, highly dispersed silica, all fillers silanized | Ba—Al borosilicat glass, SiO$_2$ particles (60 nm), SiO$_2$/SnO$_2$ core-shell particles (80 nm), all silanized |
| Particle size [µm] | 0.04-2.0 | 0.04-3.0 | 0.04-3.0 | 0.06-3.0 |
| Filler contents [wt. %] | 75.0 | 80.0 | 77.0 | 82.0 |
| Filler contents [vol. %] | 56.5 | 60.0 | 60.4 | 67.7 |
| Bending strength [MPa] (24 h/37° C., according to ISO 4049) | 118.9 (±11.2) | 116.0 (±12.5) | 132.0 (±9.0) | 145.0 (±9.0) |
| E modulus [MPa] (24 h/37° C., according to ISO 4049) | 8,150 (±385) | 8,750 (±360) | 11,100 (±300) | 11,300 (±300) |
| shrinkage [vol. %]; 30 min. value | 2.99 | 3.07 | 2.2 | 1.3 |
| x-ray opacity [% Al][4)] | 220 | 380 | ≦250 | 311 |
| abrasion[5)] | 58 | 66 | 48 | 30 |

|  | Composite 1 | Composite 2 | Composite 3 | Composite 4 |
| --- | --- | --- | --- | --- |
| Monomers | BISGMA<br>UDMA<br>TEGDMA | BISGMA[1)<br>UDMA[2)<br>TEGDMA[3) | free of monomers | free of monomers |
| Thermal expansion coeffizient α (5-50° C.) [$10^{-6} K^{-1}$] | 49.8 | 47.5 | n.a. | 26.9 |
| cytotoxicity, 3T3 cells [% vital cells after incubation time]: 24 h | 88.5 (±8.6) | 96.6 (±8.3) | 99.4 | 93.0 |
| 48 h | 93.0 (±4.1) | 86.4 (±2.1) | 98.6 | 99.6 |

[1)]2,2'-bis[4-(3'-methacryloyl-oxy-2'-hydroxylpropoxy-phenyl]propane
[2)]7,7,9-trimethyl-4,13-dioxo-3,14-dioxa-5,12-diazahexadecane-1,16-dioxy-dimethacrylate
[3)]triethyleneglycol dimethacrylate
[4)]according to ISO 4049
[5)]according to ACTA method [μm] (3 media abrasion)

The resin system upon which the composite 1 is based has a shrinkage of greater than 7% and is in this regard therefore significantly less favorable than the resin of Example 2.

A comparison of the composites 3 and 4 shows the advantages of incorporating nanoparticulate fillers into the composite: for the same resin matrix a significantly increased filler contents is possible, the strength of the composite is greater, the shrinkage is drastically reduced, the x-ray opacity is significantly increased, and the abrasion is significantly reduced.

By replacing the $SiO_2$ particles (60 nm) in composite 4 with $SiO_2/SnO_2$ particles (80 nm) the x-ray opacity can be increased from 311 to 361% Al.

The nanoparticulate filler proportion effects a significantly increased filler contents and in this connection in particular a very high volume proportion in the composite wherein the composite still enables easy application, i.e, it has an adjusted flow behavior. The results are a surprisingly significant reduction of shrinkage at 1.3% by volume in combination with a drastically reduced abrasion behavior results, a high strength, an E modulus that is approximated to that of dentine (E modulus approximately 18 GPa or in liquid approximately 10 GPa; α approximately $8*10^{-6} K^{-1}$) as well as an approximated thermal expansion coefficient, a high x-ray absorption (greater 250% Al is desired), excellent translucence (important for optical appearance of the filling), and excellent biocompatibility (according to cytotoxicity test). As demonstrated by composite 4, a monomer-free embodiment is possible which, for example, with regard to allergenic exposure already during application, i.e, in the uncured state, is of particular importance for the dental office staff.

The invention claimed is:

1. A dental composite comprising:
(A) a matrix comprising a resin with the following structural element (Ib)

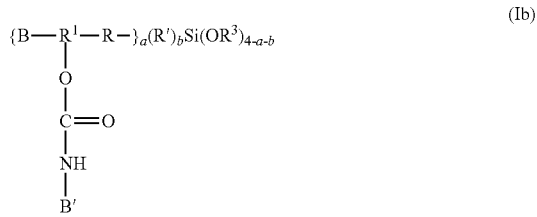

(Ib)

wherein the residues and indices have the following meaning:
R is an open-chain and/or cyclic alkylene group, arylene group, or alkylene arylene group with 1 to 10 carbon atoms, respectively, and is optionally interrupted by one or several oxygen or sulfur atoms or carboxyl or amino groups or optionally carries such atoms/groups at an end remote from the silicon atom;
$R^1$ is an open-chain and/or cyclic alkylene group, arylene group, or alkylene arylene group with 1 to 10 carbon atoms, respectively, substituted with the urethane group shown in the formula (Ib), and is optionally interrupted by one or several oxygen or sulfur atoms or carboxyl or amino groups or optionally carries such atoms/groups at one end;
R' is an open-chain and/or cyclic alkyl group, alkenyl group, aryl group, alkyl aryl group, or aryl alkyl group with preferably 1 to 20 carbon atoms;
B and B' are the same or different and have the meaning of a straight-chain or branched organically polymerizable group with at least one (meth)acrylate residue and thus at least 3 carbon atoms;
$R^3$ are the same or different, wherein at least some of the $R^3$ have the meaning of a bond to another silicon atom and, when not a bond to another silicon atom, are a hydrogen atom, an alkyl group with 1 to 10 carbon atoms, or a bond to another metal atom that can be incorporated into silicic acid hetero polycondensates;
a is 1 or 2 and b is 0 or 1; and
(B) a nanoparticulate filler; and
further comprising a polymerization initiator.

2. The dental composite according to claim 1, wherein the polymerization initiator is selected from the group consisting of initiators for radical curing, initiators for thermal curing, and initiators for radiation curing.

3. The dental composite according to claim 1, wherein at least one of B and B' contains one or two methacrylate groups or is a methacrylate residue.

4. The dental composite according to claim 1, wherein B and optionally B' are methacrylate acid ester groups of trimethylol propane, of glycerine, of pentaerythrite, of $C_2$-$C_4$ alkanediols, of polyethylene glycols, of polypropylene glycols, or of optionally substituted and/or alkoxylated bisphenol A.

5. The dental composite according to claim 1, wherein B and optionally B' comprise methacrylate acid ester groups of trimethylol propane, of glycerine, of pentaerythrite, of $C_2$-$C_4$ alkanediols, of polyethylene glycols, of polypropylene glycols, or of optionally substituted and/or alkoxylated bisphenol A or comprise these esters.

6. The dental composite according to claim 1, wherein $R^1$ is a $C_1$-$C_6$ alkylene group substituted with a urethane group.

7. The dental composite according to claim 1, wherein structural elements of the resin are comprised to at least 60 mole % of the structural elements of the formula (Ib).

8. The dental composite according to claim 1, wherein structural elements of the resin are comprised predominantly of the structural elements of the formula (Ib).

9. The dental composite according to claim 1, wherein structural elements of the resin are comprised exclusively of the structural elements of the formula (Ib).

10. The dental composite according to claim 1, wherein the nanoparticulate filler is comprised of approximately spherical particles with narrow diameter distribution or contains such spherical particles with narrow diameter distribution.

11. The dental composite according to claim 10, wherein the nanoparticulate particles have essentially a diameter between 10 nm and 200 nm.

12. The dental composite according to claim 1, further comprising an additional filler.

13. The dental composite according to claim 12, wherein the additional filler is selected from macrofillers of glass, ceramic or quartz with particle sizes between 2 µm to 50 µm; homogenous microfillers in particular of pyrogenic silica; inhomogeneous microfillers, preferably in the form of chipped polymerisates, in particular mixtures of pyrogenic silica and Ba glass or Sr glass with particle sizes in the range of approximately 1 µm to 5 µm; dental glasses with particle diameters of approximately 1 µm to 5 µm; mixtures of these fillers; hybrid fillers; or very fine hybrid fillers.

14. The dental composite according to claim 1, containing a total filler amount of between 1 wt. % and 50 wt. % consisting of the nanoparticulate filler and an optional additional filler.

15. The dental composite according to claim 14, wherein between 5 wt. % and 60 wt. % of the total filler amount is the nanoparticulate filler.

16. The dental composite according to claim 15, wherein between 29 wt. % and 35 wt. % of the total filler amount is the nanoparticulate fillers.

17. The dental composite according claim 1, containing a total filler amount between 70 wt. % and 90 wt. % consisting of the nanoparticulate filler and an optional additional filler.

18. The dental composite according to claim 17, wherein between 5 wt. % and 60 wt. % of the total filler amount is the nanoparticulate filler.

19. The dental composite according to claim 18, wherein between 29 wt. % and 35 wt. % of the total filler amount is the nanoparticulate fillers.

20. The dental composite according to claim 1, in the form of a composite material, fastening material, cement, filling material, adhesive, coating material, fissure sealant, tooth neck coating, crown or bridge material, or bonding.

* * * * *

UNITED STATES PATENT AND TRADEMARK OFFICE
CERTIFICATE OF CORRECTION

PATENT NO.         : 7,977,404 B2
APPLICATION NO.    : 11/912145
DATED              : July 12, 2011
INVENTOR(S)        : Herbert Wolter et al.

It is certified that error appears in the above-identified patent and that said Letters Patent is hereby corrected as shown below:

In the Specification

Col. 1, line 45, the text portion "overall property el" should be changed to --overall property level--.
Col. 2, line 34, the text portion "and at east one part" should be changed to --and at least one part--.
Col. 4, line 47, the text portion "In some cases. X can also be" should be changed to --In some cases, X can also be--.
Col. 10, line 16, the text portion "butoxy group, R can" should be changed to --butoxy group. R can--.
Col. 10, line 47, the text portion "silicon atom, Accordingly" should be changed to --silicon atom. Accordingly--.

Col. 24, lines 55-60, the formula to the left " 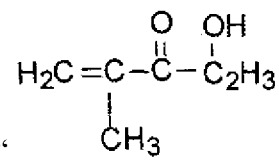 " should be changed to

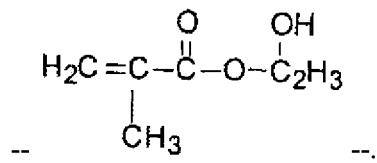

Signed and Sealed this
Twenty-fifth Day of March, 2014

Michelle K. Lee
*Deputy Director of the United States Patent and Trademark Office*